United States Patent [19]

Kanematu et al.

[11] Patent Number: 4,584,092

[45] Date of Patent: Apr. 22, 1986

[54] DEHYDRATING METHOD

[75] Inventors: Tetuo Kanematu, Himeji; Saburo Hamano, Kobe, both of Japan

[73] Assignee: Daicel Chemical Industries, Ltd., Sakai, Japan

[21] Appl. No.: 687,303

[22] Filed: Dec. 28, 1984

[30] Foreign Application Priority Data

Dec. 29, 1983 [JP] Japan ............................... 58-245775
Dec. 29, 1983 [JP] Japan ............................... 58-245776

[51] Int. Cl.$^4$ ............................................. C10G 33/04
[52] U.S. Cl. ................................... 208/188; 502/401; 502/402; 502/404
[58] Field of Search ............... 208/187, 188; 502/401, 502/402, 404

[56] References Cited

U.S. PATENT DOCUMENTS 3,215,619 11/1965 Brooke ............................... 208/187
3,417,013 12/1968 Roberts ............................... 208/188
4,345,973 8/1982 Ladish et al. ........................ 502/404
4,380,458 4/1983 Callihan ............................... 502/404

Primary Examiner—John Doll
Assistant Examiner—A. Pal
Attorney, Agent, or Firm—Flynn, Thiel, Boutell & Tanis

[57] ABSTRACT

Water is effectively removed out of an organic liquid by filtering the organic liquid with a highly water-absorptive sheet which has been prepared from an alkali metal salt of fibrous carboxymethylcellulose.

10 Claims, No Drawings

DEHYDRATING METHOD

The invention relates to a dehydrating method, that is, a method for removing water out of an organic liquid which contains water, and a filtration sheet for that purpose. Furthermore, the sheet of the invention is highly water absorptive and is suitable as material for a sanitary article.

In particular, the invention is useful for removing water which is contained in oils, or other organic liquids, by filtering the organic liquid using a highly water-absorptive sheet as filter medium.

Various petroleum fuels or lubricant oils are used widely today. Inclusion of water in such fuels or oils at the time of their use or storage, due to the condensation of moisture in the air or other reasons, is likely to cause their quality to deteriorate. The included water is sometimes present as a separate phase or emulsified. In some cases the water is even partly dissolved in the oil. Water included in oils in such various forms cannot be separated simply by means of decanting or liquid-liquid separation.

Recently, various highly water-absorptive resins have been developed which can absorb water in amounts at least ten times their own weight. If such a highly water-absorptive resin is added to the oil-containing water and the mixture is stirred, the water can be absorbed by the resin and removed. However, as these highly water-absorptive resins are in the form of finely divided powder or granules, separation of these resins from the oil, i.e. filtration is necessary after the water absorption treatment. If the material for the filter itself to be used for the filtration of oils is endowed with high water-absorptivity, oils can be treated very advantageously not only because the dehydrating process is rationalized but because various impurities can be removed at the same time.

Sheets containing highly absorptive materials have also been developed principally in the fields of sanitary goods or paper diapers. Most of these sheets have a sandwich structure in which a powdered or granular highly water-absorptive resin is interposed between sheet materials. The technical problem of these sheets at present is how to spray and fix homogeneously this powdered or granular highly water-absorptive resin and how to make the resin fully exhibit its characteristic high water absorptivity and water retentivity in the final product.

Many proposals have already been made to form the above-described highly water-absorptive resin into a sheet (see, e.g., Japanese Patent Laid-open No. 9458/1981, No. 89839/1981, or No. 91052/1981). However, since these highly water-absorptive resins are in the form of powder or granules having poor moldability, they can be used at best in the form of a sheet prepared by interposing them between pulp, paper, fiber, or other materials. As the water absorption by such pulp, paper, or fiber is based on only capillary action, not only is the amount of the water absorbed by such a sheet very small, but the degree of water retention is extremely low. It is a great disadvantage of this kind of sheet, accordingly, that the part in which very small amounts or none of the highly water-absorptive resin is contained, in a sheet inhomogeneously filled or laminated with the highly water-absorptive resin, has very low water retentivity.

A sheet comprising fibrous crosslinked CMC is disclosed in Japanese Patent Laid-open No. 26099/1981. However, this sheet has a disadvantage that expenses for the manufacturing facilities, for example, a large-scale countermeasure against solvent, are very high because water-soluble CMC must be subjected to a papermaking process in an organic solvent.

The inventors have accomplished the present invention as the result of intensive studies on the material for use as a filter for removing water contained in oils, based on the finding that a carboxymethylcellulose (Hereinafter abbreviated as CMS) sheet obtained by subjecting water-insoluble acid-type carboxymethylcellulose (hereinafter abbreviated as CMC-H) fiber to a paper making process in an aqueous system and thereafter converting it into a sodium, potassium, or other alkali metal salt can serve as a highly excellent material for use as a filter for removing the contained water.

Accordingly, the present invention provides a method for removing water contained in an organic liquid by filtering the organic liquid using a highly water-absorptive sheet as filter medium, wherein said highly water-absorptive sheet comprised of 60 to 100% by weight of an alkali metal salt of fibrous carboxymethylcellulose having a degree of substitution ranging from 0.3 to 1.0, and 40 to 0% by weight of cellulose fiber, and has a basis weight of between 20 and 300 g/m$^2$ and air permeability of not greater than 20 seconds.

The carboxymethylcellulose sheet used in the present invention can be prepared essentially by subjecting cotton-like and acid-type CMC or a mixture of it with cellulose fiber to a paper-making process in water, treating it with sodium carbonate or other alkali metal compounds to form an alkali metal salt, and heat-treating it. This is disclosed in Japanese patent publication No. 2925/67, GB 1 071 706 and GB 1 379 881. The inventors have found that the adjustment of the degree of substitution (DS) of the CMC used within the range of from 0.3 to 1.0, the basis weight from 20 and 300 g/m$^2$, and the air permeability at not greater than 20 seconds can impart to a carboxymethylcellulose sheet highly excellent water absorptivity and water retention, and that the thus prepared highly water-absorptive sheet shows outstanding characteristics as a filter for removing water contained in oils or other organic liquids.

It is preferred that the CMC composing the highly water-absorptive sheet used in the present invention has a DS ranging from 0.3 to 1.0. If the DS is smaller than 0.3, the swelling at the time of water absorption is too small to impart sufficient water retention characteristics to the filter, while if it exceeds 1.0, the CMC is eluted by water from the filter part because the solubility of the CMC in water becomes too high. The degree of polymerization of the CMC used is not particularly limited. The CMC fiber may be of any length so far as it is long enough for paper making i.e., at least about 0.5 mm.

As for the ratio of the fibrous CMC-H to the cellulose fiber, such as pulp, in the mixture for paper making, when the DS of the CMC-H is within the range of 0.3 to 0.6, the paper making process can be conducted with CMC-H only, but when the DS is within the range of 0.6 to 1.0, it is preferred from the viewpoint of manufacturing to add pulp or other cellulose fibers in an amount of at most 40% by weight, because troubles may be caused in the drainage or drying of the material under paper-making if CMC-H alone is used. The performances as a highly water-absorptive sheet for water-absorptive filter material can also be maintained by the addition of the cellulose fiber. However, when the ratio of the cellulose fiber exceeds 40% by weight, the water retention as a water-absorptive filter deteriorates.

The amount of the alkali metal compound, which is added to form an alkali metal salt, e.g. sodium carbonate, after the paper making step of the water-insoluble CMC-H fiber or a mixture of CMC-H fiber with cellulose fiber, is not limited to a stoichiometrical amount. Usually the alkali metal compound is added in an amount of 0.7 to 5 times, preferably 0.9 2 times the theoretical amount calculated from the DS. The pH value of the obtained sheet is between 6 and 12 in a product of 1% solid content. When the amount of the alkali metal compound added is too small, the water retentivity of the sheet is reduced, while if it is too large, crystals of the alkali metal compound, such as sodium carbonate, will deposit on the sheet to increase the air permeability of the sheet, thus giving a sheet which is not desirable as the material for the filter.

As the rate of the formation of an alkali metal salt of the CMC-H sheet is controlled by the penetrability of an alkali metal compound, such as sodium carbonate, into the sheet, the reaction does not always proceed homogeneously. In other words, the internal part of the sheet is likely to be converted into an alkali metal salt less rapidly than the surface. This is, however, considered rather advantageous for the characteristics of a material for a filter, because, as disclosed in Japanese Patent Laid-open No. 28755/1981 or No. 104901/1983, the CMC-H which is partly left behind in the sheet forms an ester crosslinkage, and the high water absorptivity and water retentivity of this crosslinked CMC, as well as its difficult solubility in water, prevents the elution of CMC by water from the filter part.

The basis weight of the highly water-absorptive sheet used in the present invention is preferred to be within the range of 20 to 300 g/m$^2$. When the basis weight is smaller than 20 g/m$^2$, many gaps or uneven areas are formed between the CMC fibers due to the thinness of the sheet, which may cause the leakage of water from the filter. On the other hand, when the basis weight exceeds 300 g/m$^2$, the steps of paper making or drying becomes so time-consuming that the manufacture of the sheet may be largely lowered in productivity or even becomes impossible.

As for the air permeability of the sheet, when the time necessitated for 300 ml of air to pass through two sheets exceeds 20 seconds when measured with a Gurley's Densometer, the sheet loses practical utility because the filtration resistance is too great, even in the filtration of oils including no water.

The highly water-absorptive sheet described in detail in the foregoing paragraphs can be used in single or multiple layers as a filter medium for the filtration of organic liquids. It can also be used in laminations with other sheet-like materials or in combination with other highly water-absorptive resins. As the shape of the sheet is not particularly limited, it can be used in various forms including plates, cylinders, and so on. The method of filtration can be selected from among the gravity induced filtration organic liquid, filtration under pressure, filtration under reduced pressure, pumping of the organic liquid, and any other methods.

Clean oil can be obtained advantageously by the treatment of water-containing oil using the highly water-absorptive sheet of the present invention, because the oil can be rapidly freed of water by a simple filtering operation and other solid impurities can be removed at the same time.

Another great advantage of the dehydrating method using the highly water-absorptive sheet of the present invention is that the CMC fiber composing the sheet swells as it absorbs water, making the meshes of the filter smaller. The CMC sheet of the present invention is therefore liquid-permeable when it still possesses sufficient water absorptivity, whereas the permeation of oils is spontaneously suspended when the CMC sheet loses sufficient absorptivity. It is not easy usually to check how much residual water absorptivity an absorbent has at a certain point. However, the highly water-absorptive sheet of the present invention guarantees the removal of water as long as the oils can permeate through the sheet. The highly water-absorptive sheet of the present invention can be used very conveniently because the sheet need not be exchanged until the permeation of oils is suspended.

Another advantage of the dehydrating method using the highly water-absorptive sheet of the present invention is that the sheet has sufficiently large tensile or bending strength to endure fluting, embossing, or other molding process, in spite of the extreme thinness of each sheet, which is between 0.05 and 1.0 mm.

Since CMC, which is a component of the highly water-absorptive sheet used in the present invention, and cellulose, which may optionally be incorporated in it, are both inert to hydrocarbon oils and most of organic solvents, the qualities of the oils are not disadvantageously affected by treatment with the highly water-absorptive sheet of the present invention.

As described above, the dehydrating method using the highly water-absorptive sheet of the present invention can be applied to remove water or dust from fuels for aircrafts and automobiles, kerosene, heavy fuel oil, machine oil, and other general organic solvents. Since CMC and cellulose are both approved by the standard of food additives and harmless to human body, the sheet of the present invention can also be used for the dehydration of edible oil.

Partly acid-form heat-crosslinked CMC disclosed in Japanese Patent Laid-open No. 28755/1981 or No. 104901/1983 is very suitable for the highly water-absorptive resin used in the present invention. This heat-crosslinked CMC is characterized by requiring no crosslinking agent as the third component, resulting in a great advantage of freedom from regulations by the standards of food additives and the Pharmacopoeia of Japan in the application. The heat-crosslinked CMC may be in the form of powder, granule, or short fiber, but the powdered or granular form is preferred because the short fiber is difficult to quantitatively supply for laminating. Various other recently developed highly water-absorptive resins, such as starch, acrylic acid, or PVA resins, can be used, too.

The highly water-absorptive resin used in the present invention is added in greater amounts when it is used for filtration under higher pressures, and in smaller amounts for filtration under lower pressures. In general, 10 to 1000 g/m$^2$, preferably 50 to 300 g/m$^2$ of the resin is added. If the amount of the resin is less than 10 g/m$^2$, the water retention is unsatisfactory, while if it exceeds 1000 g/m$^2$, the strength or morphological stability of the sheet is deteriorated because the integrity of the composite sheet is lowered.

The other component of the sheet used in the present invention may be ordinary paper comprising pulp or cellulose, tissue pulp, or nonwoven cloth comprising synthetic polymers. These materials are used for improving the feeling or applicability of the product, fixing the highly water-absorptive resin more steadily, or giving specified characteristics suited for various applications.

The highly water-absorptive sheet of the present invention, as a composite of the above components is prepared by, for example, spraying heat-crosslinked CMC onto a CMC sheet, laminating another CMC sheet, cellulose paper, or nonwoven cloth on the CMC sheet like a sandwich, spraying water or water vapor thereon, and roll-drying it. The sheet can also be prepared by spraying thereon an acrylic emulsion or an aqueous solution of an ordinary water-soluble polymer, in place of water or water vapor, or by immersing it in said emulsion or polymer solution. The sheet can also be strongly fixed by an embossing roller or other mechanical means. The structural unit of the sheet is not necessarily one layer. Two or three layers can be laminated.

A great advantage of the highly water-absorptive sheet of the present invention is that, for example, in the filtration of water-containing oils, the resin such as heat-crosslinked CMC and the CMC sheet swell as they absorb water, making the meshes of the filter smaller. The highly water-absorptive sheet of the present invention is therefore liquid-permeable when it still holds sufficient water absorptivity, whereas the permeation of oils is spontaneously suspended when it loses sufficient water absorptivity. It is not easy usually to check how much residual water absorptivity a water absorbent has at a certain point. However, the highly water-absorptive sheet of the present invention guarantees the removal of water as long as the oil can permeate through the sheet. The highly water-absorptive sheet of the present invention can be used very conveniently because the sheet need not be exchanged until the permeation of the oil is suspended, or when the filter pressure is elevated.

Another outstanding characteristics of the highly water-absorptive sheet of the present invention, which distinguishes it from conventional water-absorptive materials, is that the CMC sheet, used in place of conventional tissue pulp or ordinary paper on at least one or both of the surfaces of the highly water-absorptive resin to sandwich it, can rapidly absorb and retain water which the highly water-absorptive resin has failed to absorb or retain. The sheet of the present invention is, therefore, free from the fear of water leakage even if rapid filtration is made under high pressures.

Moreover, a great disadvantage of conventional water-absorptive materials has been extremely low absorptivity and retentivity of aqeuous solutions which contain small amounts of salts, no matter how excellent characteristics these materials have shown in the absorption and retention of pure water. The highly water-absorptive sheet of the present invention shows characteristically high absorptivity and retentivity in the absorption of aqueous solutions containing various salts, as well as blood or urine.

As described above, the highly water-absorptive sheet of the present invention is useful as the filter material for removing water or dust from fuels for aircrafts and automobiles, kerosine, heavy fuel oil, machine oil, edible oil, and other general organic solvents, as the water-absorptive material for paper diapers, menstrual sanitary goods, bed pads, paper towels, and other sanitary or disposable goods, and as the material for dehumidifying air filters, dehumidifying sheet material, drying agents for food, or various waterproof coating materials.

The present invention will be described in more detail by the following examples, but these examples are not intended to limit the scope of the present invention.

The fundamental physical characteristics of the sheet were measured according to the following methods:

| basis weight: | JIS P 8124 |
| tensile strength: | JIS P 8113 |
| air permeability: | JIS P 8117 |
| thickness: | JIS P 8118 |

Although the air permeability is expressed by the time necessitated for 100 ml of air to pass through one sample sheet according to JIS, the measurement conditions were partly altered in the application of the present invention, i.e. the air permeability was expressed by the time necessitated for 300 ml of air to pass through two sample sheets.

EXAMPLE 1

Cotton-like CMC-H having a DS of 0.45 was disintegrated in water, subjected to a paper making process and preliminarily dried to form a CMC-H sheet. The obtained CMC-H sheet was immersed in a bath comprising 10% by weight of sodium carbonate, 3% by weight of glycerol, and 87% by weight of water, and then dried to prepare a CMC sheet. The obtained CMC sheet had a basis weight of 70 g/m$^2$, a thickness of 0.12 mm, an air permeability of 1.0 seconds, and a tensile strength of 2.5 kg/15 mm width.

The water-absorptivity of this CMC sheet in gas oil was measured by cutting the sheet into circular pieces of 140 mm in diameter, inserting two of these pieces, one over the other, between two sheets of filter paper (Toyo filter paper No. 5A), setting it in the filter part of a pressure filter, supplying water-containing gas oil, and filtering it under air pressure. The water-containing gas oil was one prepared by mixing 20 ml of water with 500 ml of the oil before the filtration. As the result of the filtration under pressure, no separated water was recognized at all in the filtrate. The amount of water dissolved in the filtered gas oil was 40 ppm as measured by the Karl Fischer method.

COMPARATIVE EXAMPLE 1

500 ml of gas oil containing 20 ml of separated water as in Example 1 was placed in a pressure filter provided with two sheets of filter paper only, without the CMC sheet of the present invention, and filtered. It was recognized after the filtration that about 20 ml of the separated water remained in the filtered gas oil with no changes. The amount of water dissolved in the gas oil measured after the treatment was 120 ppm.

EXAMPLE 2

The same CMC sheet as used in Example 1 was set in a pressure filter, with which 500 ml of gas oil containing 20 ml of separated water was filtered. Another 500 ml of gas oil containing 20 ml of separated water was then provided in the filter for filtration, but the additionally provided gas oil could not be filtered at all even if the air pressure was raised to 3 kg/cm$^2$. This suggested that the CMC sheet which had absorbed water to its saturation point clogged the meshes of the filter by swelling, and functioned to suspend the permeation of the gas oil itself.

EXAMPLE 3

The same CMC sheet as used in Example 1 was set in a pressure filter to treat Daphne oil No. 56 (lubricant oil manufactured by Idemitsu Kosan). The amount of water dissolved in the oil before the treatment was 20 ppm, while the one after the treatment was 0.6 ppm.

EXAMPLE 4

The filtration was carried out in the same manner as described in Example 3 except that methyl isobutyl ketone containing separated water was used as the organic solvent to be treated. No separated water was observed in the filtrate obtained after the treatment.

EXAMPLE 5

A mixture of 80 parts by weight of cotton-like CMC-H having a DS of 0.45 and 20 parts by weight of beaten pulp for the manufacture of paper was disintegrated in water, subjected to a paper making process and converted into a sodium salt in the same manner as described in Example 1 to obtain a CMC-pulp mixture sheet. The obtained sheet had a basis weight of 120 g/m$^2$, a thickness of 0.2 mm, an air permeability of 4.1 seconds, and a tensile strength of 5.6 kg/15 mm width.

The water-absorptivity as the material for the filter of this sheet was measured in the same manner as described in Example 1 using the same water-containing gas oil. The adhesion onto the walls of the container of a very slight amount of the separated water in drops was observed in about 500 ml of the gas oil after the filtration, but the amount of these water drops was as small as about 0.05 ml or less. The amount of water dissolved in the filtrate was 70 ppm.

EXAMPLE 6

A mixture of 80 parts by weight of cotton-like CMC-H having a DS of 0.65 and 20 parts by weight of beaten pulp for the manufacture of paper was formed into a mixture sheet in the same manner as described in Example 5. The obtained CMC mixture sheet had a basis weight of 120 g/m$^2$, a thickness of 0.24 mm, and an air permeability of 1.0 second.

The water absorptivity of this sheet was measured in the same manner as described in Example 1 using water-containing gas oil. No separated water was observed in the gas oil after the filtration, and the amount of water dissolved in the oil was 30 ppm.

EXAMPLE 7

A mixture of 70 parts by weight of cotton-like CMC-H having a DS of 0.85 and 30 parts by weight of beaten pulp for the manufacture of paper was formed into a mixture sheet in the same manner as described in Example 5. The obtained CMC mixture sheet had a basis weight of 140 g/m$^2$, a thickness of 0.26 mm, and an air permeability of 1.2 second.

The water absorptivity of this sheet was measured in the same manner as described in Example 1 using water-containing gas oil. No separated water was observed in the gas oil after the filtration, and the amount of water dissolved in the oil was 50 ppm.

EXAMPLE 8

Heat-crosslinked CMC, i.e. a highly water-absorptive resin, was prepared by heat-treating granular CMC having a DS in the form of a sodium salt of 0.75, a DS in the acid form of 0.01, and a particle size ranging from 30 to 80 mesh, at 140° C. for 1 hour according to the method described in Japanese Patent Laid-open No. 104901/1983.

Separately, a CMC sheet was prepared by forming CMC-H paper by the disintegration in water, papermaking, and preliminarily heating of cotton-like CMC-H having a DS of 0.45, immersing the obtained CMC-H paper in a bath comprising 10% by weight of sodium carbonate, 3% by weight of glycerol, and 87% by weight of water, and drying it. The obtained CMC sheet had a basis weight of 70 g/m$^2$, a thickness of 0.12 mm, an air permeability of 1.0 second, and a tensile strength of 2.5 kg/15 mm width.

The heat-crosslinked CMC was laminated between two sheets of the CMC sheet prepared by the above-described process. Water vapor was sprayed on the laminated sheet, which was then dried with a heat roll to form a sample water-absorptive sheet containing the heat-crosslinked CMC in an amount of 150 g/m$^2$.

The obtained laminated water-absorptive sheet had a basis weight of 280 g/m$^2$ and a thickness of 0.4 mm. The water-absorptivity of this sheet in gas oil was measured by cutting the sample sheet into circles of 140 mm in diameter, setting it in the filter part of a pressure filter, supplying water-containing gas oil in the filter, filtering the oil under pressure with air, and determining the water content in the filtrate.

The gas oil to be filtered had been mixed with water in a proportional amount of 20 ml of water in 500 ml of the oil per batch.

The filtration was completed at a filtration pressure with air not greater than 0.5 kg/cm$^2$ and a filtration time within 1 minute per batch. No separated water was recognized at all in about 500 ml of the filtered gas oil. The amount of water dissolved in this filtered gas oil was 20 ppm according to the result of the measurement by means of the Karl Fischer method. The amount of water dissolved in the gas oil before the filtration had been 130 ppm.

COMPARATIVE EXAMPLE 2

The laminated sheet was prepared in the same manner as described in Example 8 except that two sheets of pulp in the form of tissue paper were used in place of two sheets of the CMC sheet.

This tissue paper had a basis weight of 35 g/m$^2$ and a thickness of 0.1 mm.

The water-absorptivity of the sheet in which heat-crosslinked CMC was laminated on this tissue paper was measured in the same manner as described in Example 8.

The filtration under pressure was completed at a pressure not greater than 0.5 kg/cm$^2$ and a filtration time within 1 minute, but about 2 ml of separated water was recognized in about 500 ml of the filtered gas oil. The amount of water dissolved in this filtered gas oil was 100 ppm.

EXAMPLE 9

The same water-absorptive sheet as used in Example 8 was set in a pressure filter and Daphne oil (lubricant oil manufactured by Idemitsu Kosan) No. 56 was used as the oil to be treated. The amount of water dissolved in the Daphne oil before the treatment was 20 ppm, while that after the treatment was 0.4 ppm.

EXAMPLE 10

The same water-absorptive sheet as used in Example 8 was set in a pressure filter, and 500 ml of salad oil for domestic use (manufactured by Nisshin Seiyu) to which 10 ml of water had been added was used as the oil to be treated. No separated water was recognized at all in the filtered salad oil.

EXAMPLE 11

The same water-absorptive sheet as used in Example 8 was set in a pressure filter, and 500 ml of methyl isobutyl ketone to which 10 ml of water had been added was used as the organic solvent to be treated. No separated water was recognized at all in the filtered ketone.

EXAMPLE 12

A sheet in which 450 g/m$^2$ of heat-crosslinked CMC was laminated in the CMC sheet obtained in Example 8 was prepared. The water-absorptivity of this sheet in water-containing gas oil was measured in the same manner as described in Example 8. No separated water was recognized at all in the filtered gas oil. The amount of water dissolved in the filtered gas oil was 10 ppm.

EXAMPLE 13

The same water-absorptive sheet as used in Example 8 was set in a pressure filter and the first batch of 500 ml of gas oil including 20 ml of separated water was filtered. After the filtration was completed at the same filtration pressure and time as in Example 8, the second batch of 500 ml of gas oil including 20 ml of water was continuously filtered through the same sheet. The second filtration was also completed at a filtration pressure not greater than 0.5 kg/cm$^2$ and a filtration time within 1 minute. No separated water was recognized at all in the filtered gas oil. The third batch of 500 ml of gas oil including 20 ml of water was then supplied to the filter for further filtration, but the oil could never be filtered even at a filtration pressure of as high as 3 kg/cm$^2$.

It was apparent from this result that the heat-crosslinked CMC and the CMC sheet had absorbed water to its saturation point, clogging the meshes of the filter by swelling, and functioned to suspend the permeation of the gas oil itself.

EXAMPLE 14

A water-absorptive sheet in which heat-crosslinked CMC was laminated between one sheet of the CMC sheet used in Example 8 and one sheet of the tissue paper used in Comparative Example 2, in place of two CMC sheets, was prepared. The water-absorptivity of this sheet was measured in the same manner as described in Example 8. No separated water was recognized at all in the gas oil filtered under pressure, and the amount of water dissolved in this filtered gas oil was 27 ppm.

EXAMPLE 15

The liquid absorptivity of the water-absorptive sheet obtained in Example 8 was measured by the following method, using pure water and a 1% saline solution. The sheet cut into a square of 20×20 mm was immersed in 200 ml of pure water or a 1% saline solution for 30 minutes at room temperature, slowly stirred, and poured into a centrifugation tube provided with a gauze for centrifugal separation. An 80-mesh gauze (a cylinder of 25 mm in diameter and 60 mm in height) had been set inside of this centrifugation tube so that the liquid flowing out during the centrifugation was separated from the sample. The samples were centrifugally separated for 5 minutes at a centrifugal force of 500 G. After the centrifugation, the weight of the sample remaining on the gauze (w1) was measured, and the oven-dry weight of the sample was measured after it was dried at 105° C. (W2). The centrifugal liquid retention ratio (W1−W2/W2) was calculated from these values.

The centrifugal liquid retention ratio of the water-absorptive sheet obtained in Example 8 was 210 with pure water, and 70 with a 1% saline solution.

COMPARATIVE EXAMPLE 3

For the comparison with the results of Example 15, the liquid absorptivity of a sheet in which a commercially available highly absorptive resin (starch resin) was laminated between two sheets of the tissue paper used in Comparative Example 2 was measured in the same manner as described in Example 15. The basis weight (the amount of the sheet added) was the same as that of the water-absorptive sheet used in Example 15.

The centrifugal liquid retention ratio of this sheet for comparison was 180 with pure water, and 13 with a 1% saline solution.

The embodiments of the invention in which an exclusive property or privilege is claimed are defined as follows:

1. A method for removing water from an organic liquid that contains water, which comprises flowing said organic liquid through a sheet of porous filter paper consisting essentially of from 0 to 40 percent by weight of cellulose fibers and from 60 to 100 wt.% of fibers of an alkali metal salt of carboxymethylcellulose whereby to cause the water to be absorbed by said alkali metal salt of carboxymethylcellulose, said alkali metal salt of carboxymethylcellulose having a degree of substitution of from 0.3 to 1.0, and said sheet having a basis weight of from 20 to 300 g/m$^2$ and an air permeability of not greater than 20 seconds.

2. A method as claimed in claim 1 in which said sheet has a thickness of from 0.05 to 1.0 mm.

3. A method as claimed in claim 1 in which said sheet consists of fibers of said alkali metal salt of carboxymethylcellulose having a degree of substitution of from 0.3 to 0.6.

4. A method as claimed in claim 1 in which said sheet consists of a blend of said cellulose fibers and said fibers of said alkali metal salt of carboxymethylcellulose having a degree of substitution of from 0.6 to 1.0.

5. A method as claimed in claim 1 in which said sheet of porous filter paper has been prepared by forming a preliminary sheet from an aqueous slurry of water-insoluble acid-type carboxymethylcellulose fibers or mixture thereof with cellulose fibers, by a paper making process, then applying an alkali metal compound to said preliminary sheet in an amount in the range of from 0.7 to 5 times the amount that is required to neutralize said acid-type carboxymethylcellulose whereby to convert said acid-type carboxymethylcellulose to alkali metal salt of carboxymethylcellulose and to obtain said sheet of porous filter paper which has a pH of from 6 to 12.

6. A method as claimed in claim 5 in which said alkali metal compound is sodium carbonate and said sodium carbonate is applied to said preliminary sheet by immersing said preliminary sheet into an aqueous bath of sodium carbonate.

7. A method for removing water from an organic liquid that contains water, which comprises flowing said organic liquid through a porous filter medium comprising a sheet-form assembly of two sheets having a layer of highly water-absorptive resin therebetween, at least one of said two sheets being a sheet of porous filter paper made of an alkali metal salt of carboxymethylcellulose.

8. A method as claimed in claim 7 in which said one sheet of porous filter paper consists essentially of from 0 to 40 percent by weight of cellulose fibers and from 60 to 100 wt.% of fibers of an alkali metal salt of carboxymethylcellulose whereby to cause the water to be absorbed by said alkali metal salt of carboxymethylcellulose and said highly water-absorptive resin, said alkali metal salt of carboxymethylcellulose having a degree of substitution of from 0.3 to 1.0, and said one sheet having a basis weight of from 20 to 300 g/m$^2$ and an air permeability of not greater than 20 seconds.

9. A method as claimed in claim 7 in which said highly water-absorptive resin between said two sheets is a partly acid-form heat-crosslinked carboxymethylcellulose.

10. A method as claimed in claim 7 in which the amount of said highly water-absorptive resin is from 10 to 1,000 g/m$^2$.

* * * * *